United States Patent [19]
Steinhardt et al.

[11] Patent Number: 5,559,004
[45] Date of Patent: Sep. 24, 1996

[54] METHODS FOR SCREENING COMPOUNDS TO DETERMINE CALCIUM LEAK CHANNEL INHIBITION ACTIVITY

[75] Inventors: Richard A. Steinhardt, Berkeley; Varghese John; Lawrence C. Fritz, both of San Francisco, all of Calif.

[73] Assignees: The Regents of the University of California, Berkeley; Athena Neurosciences, Inc., So. San Francisco, both of Calif.

[21] Appl. No.: 273,666

[22] Filed: Jul. 12, 1994

[51] Int. Cl.$^6$ .................................................. C12Q 1/02
[52] U.S. Cl. .................................................. 435/29; 435/968
[58] Field of Search .......................... 435/29, 69.2, 184, 435/968

[56] References Cited

U.S. PATENT DOCUMENTS

| | | | |
|---|---|---|---|
| 4,771,057 | 9/1988 | Knaus et al. | 514/334 |
| 4,950,739 | 8/1990 | Cherksey | 530/350 |

OTHER PUBLICATIONS

Mongini T., Free Cytoplasmic Ca$^{+2}$ at Rest . . . Neurology 38 1908 pp. 476–480.
Wei, X., Voltage–Dependent Binding of . . . Mol Pharmacology 35 (1989) pp. 541–552.
Pang P., Control of Calcium Channels in . . . Exp Gerontology 25 pp. 247–253 (1990).
Fong P., Increased Activity of Calcium Leak . . . Science 250: 673–676 (1990).
Wang Y., Effect of Serotonin on Intracellular . . . Can J Physiol Pharmacol 69 1991 pp. 393–399.
Turner et al. (1988), Nature, 335:735–738.
Fong et al. (1990), Science, 250:673–676.
Coulombe et al. (1989), J. Membrane Biol., 111:57–67.
Turner et al. (1991), J. Cell Biol., 115:1701–1712.
Guengerich et al. (1991), J. Med. Chem. 34:1838–1844.
Bertorini, et al., "Calcium and magnesium content in fetuses at risk and prenecrotic Duchenne muscular dystrophy," *Neurology*, 34:1436–1440 (1984).
Ferrante, et al., "Homologous and heterologous regulation of voltage–dependent calcium channels," *Biochemical Pharmacology*, 39;8:1267–1270 (1990).
Ferrante, et al., "Drug– and Disease–Induced Regulation of Voltage–Dependent Calcium Channels," *Pharmacological Reviews*, 42;1:29–44 (1990).
Fingerman, et al., "Defective Ca$^{2+}$ metabolism in Duchenne muscular dystrophy: Effects on cellular and viral growth," *Proc. Natl. Acad. Sci.*, 81:7617–7621 (1984).
Fong, et al., "Increased Activity of Calcium Leak Channels in Myotubes of Duchenne Human and *mdx* Mouse Origin," *Science*, 250:673–676 (1990).
Galletti, et al., "1,4—Dihydropyridine activators in the tiamdipine series," *European Journal of Pharmacology*, 185:157–161 (1990).
Galletti, et al., "Interactions of analogs of the 1,4—dihydropyridine tiamdipine in cardiac and smooth muscle," *European Journal of Pharmacology*, 195:125–129 (1991).

Gengo, et al., "In vito and in vivo characterization of 2,6—dimethyl—3,5—dicarbomethoxy—4—(2—isothiocyano)phenyl—1,4—dihydropyridine as a Ca$^{2+}$ channel antagonist," *Can. J. Physiol. Pharmacol.*, 65:2472–2482 (1987).
Joslyn, et al., "Dimeric 1,4—Dihydropyridines as Calcium Channel Antagonists," *Journal of Medicinal Chemistry*, 31:1489–1482 (1988).
Kwon, et al., "Pharmacologic and radioligand binding analysis of the actions of 1,4—dihydropyridine activators related to Bay K 8644 in smooth muscle, cardiac muscle and neuronal preparations," *Naunyn–Schmiedeberg's Archives of Pharmacology*, 339:19–30 (1989).
Kwon, et al., "The interactions of 1,4—dihydropyridines bearing a 2—(2—aminoethylthio)methyl substituent at voltage–dependent Ca$^{2+}$ channels of smooth muscle, cardiac muscle and neuronal tissues," *Naunyn–Schmiedeberg's Archives of Pharmacology*, 341:128–136 (1990).
Mongini, et al., "Free cytoplasmic Ca$^{++}$ at rest and after cholinergic stimulus is increased in cultured muscle cells from Duchenne muscular dystrophy patients," *Neurology*, 38:476–480 (1988).
Rampe et al., "New ligands for L-type Ca$^{2+}$ channels," *Trends in Pharmacological Sciences*, 11:112–115 (1990).
Taylor, et al., "2—(2—Aryl—2—oxoethylidene)—1,2,3, 4— tetrahydropyridines. Novel Isomers of 1,4—Dihydropyridine Calcium Channel Blockers," *Journal of Medicinal Chemistry*, 31;8:1659–1664 (1988).
Triggle, "Endogenous Ligands for the Calcium Channel: Myths and Realities," *The Calcium Channel: Structure, Function and Implications*, edited by Morad, Nayler, Kazda, Schramm, 549–563 (1988).
Triggle et al., "Calcium Channels in Smooth Muscle Properties and Regulations," *Annals of the New York Academy of Sciences*, 560:215–229 (1989).
Triggle et al., "Ca$^{2+}$ Channel Ligands: Structure–Function Relationships of The 1,4—Dihydropyridines," *Medicinal Research Reviews*, 9;2:123–180 (1989).
Triggle, "Calcium Antagonists," *Cardiovascular Pharmacology*, 3rd ed. edited by Antonaccio, 107–160 (1990).

(List continued on next page.)

*Primary Examiner*—Ralph J. Gitomer
*Attorney, Agent, or Firm*—Townsennd and Townsend and Crew LLP

[57] ABSTRACT

Intracellular free calcium concentrations are lowered by administering certain dihydropyridine derivatives to cells. Dihydropyridine and other test compounds are screened for their ability to lower intracellular free calcium, particularly by inhibiting the influx of calcium through calcium leak channels, and the identified compounds incorporated into pharmaceutical compositions. Exemplary dihydropyridine derivative compounds include 4-(3-trifluoromethylphenyl)-2,6-dimethyl-3,5-dicarbomethoxy-1,4-dihydropyridine; 4-(4-bromophenyl)-2,6-dimethyl-3,5-dicarbomethoxy-1,4-dihydropyridine; 4-(4-trifluoromethylphenyl)-2,6-dimethyl-3,5-dicarbomethoxy-1,4-dihydropyridine; 4-(4-methylphenyl)-2,6-dimethyl-3,5-dicarbomethoxy-1,4-dihydropyridine; and 4-(4-cyanophenyl)-2,6-dimethyl-3,5-dicarbomethoxy-1,4-dihydropyridine.

4 Claims, No Drawings

OTHER PUBLICATIONS

Triggle, "Calcium Antagonists History and Prospective," *Stroke*, 21;12:IV-49–58 (1990).

Turner, et al., "Increased protein degradation results from elevated free calcium levels found on muscle from *mdx* mice," *Nature*, 335:735–738 (1988).

Turner, et al., "Increased Calcium Influx in Dystrophic Muscle," *The Journal of Cell Biology*, 115;6:1701–1712 (1991).

Wei, et al., "Pharmacologic and Radioligand Binding Analysis of the Actions of 1,4—Dihydropyridine Activator–Antagonist Pairs in Smooth Muscle," *The Journal of Pharmacology and Experimental Therapeutics*, 239;1:144–153 (1986).

Wei, et al., "Voltage–Dependent Binding of 1,4—Dihydropyridine $Ca^{2+}$ Channel Antagonists and Activators in Cultured Neonatal Rat Ventricular Myocytes," *Molecular Pharmacology*, 35:541–552 (1989).

Wei, et al., "$Ca^{2+}$ channels in chick neural retina cells characterized by 1,4—dihydropyridine antagonists and activators," *Can. J. Physiol. Pharmacol.*, 67:506–514 (1989).

METHODS FOR SCREENING COMPOUNDS TO DETERMINE CALCIUM LEAK CHANNEL INHIBITION ACTIVITY

This invention was made with Government support under Grant Contract No. AR41129-01 awarded by the National Institutes of Health. The Government has certain rights in this invention.

BACKGROUND OF THE INVENTION

1. Field of the Invention

The present invention relates generally to methods for lowering intracellular free calcium levels, and more particularly to methods and pharmaceutical compositions for lowering intracellular free calcium levels in mammalian hosts.

Elevated intracellular free calcium levels are associated with a number of pathogenic conditions, such as muscular dystrophy, hypertension, traumatic brain injury, stroke, Alzheimer's disease, and the like. It would be desirable to identify active compounds, pharmaceutical compositions, and methods which are capable of lowering intracellular free calcium levels and at least partially alleviating such conditions.

2. Description of the Background Art

Dystrophic conditions in mouse muscle fibers have been associated with elevated free intracellular calcium levels (Turner et al. (1988) Nature 335:735–738), and such elevated calcium levels have been associated with enhanced calcium influx through calcium ($Ca^{+2}$) leak channels (Fong et al. (1990) Science 250:673–676). Coulombe et al. (1989) J. Membr. Biol. 111:57–67, reported that compound Bay K 8644 increased activity in cardiac calcium leak channels. Turner et al. (1991) J. Cell Biol. 115:1701–1712, reported that nifedipine (4-( 2'-nitrophenyl-2,6-dimethyl-3,5-dicarboxymethyloxy-1,4 -dihydropyridine) increases calcium leak channel activity and intracellular free calcium in dystrophic mouse (mdx) skeletal muscle fibers and myotubes and human Duchenne muscular dystrophy myotubes, and predicted that any agent that would significantly reduce leak channel activity will result in lowered free intracellular calcium concentrations. Compound Bay K 8644 and nifedipine are both dihydropyridine compounds. Dihydropyridines are known to modulate the activity of L-channels, a class of calcium channels distinct from leak channels.

U.S. Pat. No. 4,771,057 and Guengerich et al. (1991) J. Med. Chem. 34:1838–1844, describe the preparation of various dihydropyridine derivatives, including 4-(3'-trifluoromethylphenyl)-2,6-dimethyl-3,5 -dicarbomethoxy-1,4-dihydropyridine.

The full disclosures of each of these background references are incorporated herein by reference.

SUMMARY OF THE INVENTION

According to the present invention, methods for lowering intracellular free calcium comprise administering to cells an amount of a compound effective to lower said intracellular free calcium, where the compound has usually been selected to decrease calcium leak channel activity. Useful compounds include certain dihydropyridine derivatives, and screening assays are provided which measure the accumulation of intracellular free calcium. Useful compounds particularly include those found capable of inhibiting leak channel activity and thus inhibiting calcium influx, resulting in a decrease in calcium accumulation.

The present invention further provides methods for treating a mammalian host, particularly human hosts, to lower intracellular free calcium levels, particularly in order to treat pathological conditions associated with elevated intracellular free calcium levels, such as muscular dystrophy, hypertension, traumatic brain injury, stroke, Alzheimer's disease, and the like.

The present invention still further comprises pharmaceutical compositions comprising a compound selected to inhibit calcium leak channel activity and a pharmaceutically acceptable carrier, where the compound is present in the carrier in an amount effective to lower intracellular free calcium levels when administered to a mammalian host.

DESCRIPTION OF SPECIFIC EMBODIMENTS

The methods and compositions of the present invention are based on the discovery that certain compounds can lower intracellular free calcium levels ($[Ca^{+2}]$) in cells and hosts, where the compounds appear to act by inhibiting the activity of cellular calcium leak channels which permit calcium influx and accumulation of intracellular calcium. In particular, it has been found that certain dihydropyridine derivatives are able to inhibit leak channel activity in dystrophic and other cells. While common dihydropyridines, such as nifedipine and nitrendipine, have previously been found to enhance leak channel activity in cells (resulting in increased calcium influx and accumulation), other dihydropyridine derivatives have now been identified which appear to inhibit leak channel activity and which are able to lower intracellular calcium concentrations.

A wide variety of compounds and substances may be utilized for inhibiting calcium leak channel activity and lowering intracellular calcium concentrations according to the methods of the present invention. Suitable compounds may include peptidic and non-peptidic small molecules, proteins, polypeptides, carbohydrates, and the like, which will display the desired calcium leak channel inhibition when administered to cells or host at appropriate concentrations and under appropriate conditions. Screening assays to identify such compositions will be described in greater detail hereinafter.

Particularly useful will be para-substituted or meta-substituted dihydropyridine (DHP) compounds having the formula I:

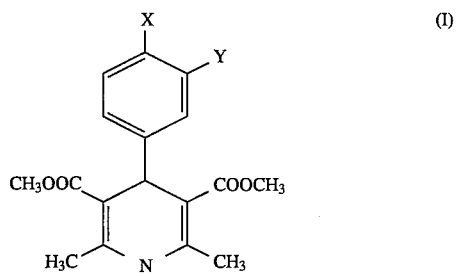

where X is hydrogen, methyl, ethyl, butyl, trifluoromethyl, O-benzyl, dimethylamino, nitro, fluoro, chloro, bromo, iodo, cyano or thiocyanate, and where Y is hydrogen, trifluoromethyl, O-benzyl, cyano or thiocyanate. Preferably, X is hydrogen, methyl, trifluoromethyl, O-Benzyl, dimethylamino, bromo or cyano groups, and Y is hydrogen or trifluoromethyl; or a pharmaceutically acceptable salt of said compound. Usually, the compounds will not be substituted at both the para and meta positions. In a first exemplary leak channel inhibiting compound, X is hydrogen and Y is trifluoromethyl, where the compound is 4-(3-trifluoromethylphenyl)-2,6-dimethyl-3,5-dicarbomethoxy-1,4-dihyropyridine. In a second exemplary leak channel inhibiting compound, X is trifluoromethyl and Y is hydrogen, where the compound is 4-(4-trifluoromethylphenyl)-2,6-dimethyl-3,5-dicarbomethoxy-1,4-dihydropyridine. In a third exemplary leak channel inhibiting compound, X is bromo and Y is hydrogen, where the compound is 4-(4-bromophenyl)-2,6-dimethyl-3,5-dicarbomethoxy-1,4-dihyropyridine. In a fourth exemplary leak channel inhibiting-compound, X is methyl and Y is hydrogen, where the compound is 4-(4-methylphenyl)-2,6-dimethyl-3,5-dicarbomethoxy-1,4-dihyropyridine. In a fifth exemplary leak channel inhibiting compound, X is cyano and Y is hydrogen, where the compound is 4-(4-cyanophenyl)-2,6-dimethyl-3,5-dicarbomethoxy-1,4-dihydropyridine.

Pharmaceutically acceptable salts are those salts of the DHP compounds which retain biological effectiveness and properties of the parent compound, which are biologically acceptable to treated hosts, and which do not possess other properties which render them unsuitable for pharmaceuticals. The preparation of pharmaceutically acceptable salts from parent compounds is well known in the pharmaceutical arts, as described in Remington's Pharmaceutical Sciences, infra.

Methods for preparing such substituted dihydropyridine compounds are well described in the scientific and patent literature. See, for example, Guengerich et al., (1991) *J. Med. Chem.* 34:1838–1844, and U.S. Pat. No. 4,771,057, the disclosures of which are incorporated herein by reference. The preparation of 4-(4'-trifluoromethylphenyl)-2,6-dimethyl-3,5-dicarbomethoxy-1,4-dihydropyridine in particular is described in Example 14 of U.S. Pat. No. 4,771,057.

The present invention also provides methods for testing such substituted dihydropyridine compounds, and other test compounds, for activity in lowering intracellular free calcium levels, particularly by decreasing calcium leak channel activity. In general, the tests measure intracellular free calcium levels in cultured cells, which may be normal or dystrophic cells, preferably being dystrophic cells. Such tests may further measure leak channel activity directly, as described in more detail below. Suitable cells for testing in vitro include myotubes, muscle fiber cells, neurons, and the like, particularly preferably being myotubes which are multinucleated and elongated without any branching. Myotubes should be uniform in width along their entire length and be at least 20 μm wide and 100 μm long.

The cells will be cultured under conditions selected to permit measurement of resting levels of free intracellular calcium ($Ca^{+2}$), where intracellular calcium levels are at least partly dependent on calcium leak channel activity. Suitable culture conditions are set forth in detail in the experimental section hereinafter.

The intracellular calcium level in such cultured cells is measured in the presence and in the absence of a test compound, and test compounds which are found to lower free intracellular calcium levels are considered to be suitable candidates for use in the methods and compositions of the present invention. Usually, an initial or baseline concentration of intracellular calcium will be established and, thereafter, the test compound will be added to the culture medium at a concentration considered likely to be effective to affect intracellular calcium levels. Typically, the compound will be added to a concentration in the range from about 1 nM to 1 mM, usually being in the range from about 100 nM to 0.01 mM. The intracellular calcium levels may then be periodically measured over a predetermined time period in order to determine the activity of the test compound. Typically, intracellular calcium concentration measurements will be made every 5 to 30 minutes over a time period in the range from 15 min. to several hours.

One method for measuring intracellular calcium levels in cultured cells is described in detail in the Experimental section hereinafter. Briefly, the cells are cultured in the presence of a calcium-sensitive dye precursor, such as an acetoxymethyl ester of fura-2, available from Molecular Probes, Inc., Eugene, Oreg. The cells take up the precursor, and the precursor is intracellularly hydrolyzed to produce fura-2 which is a calcium chelator whose fluorescent properties change when bound to calcium. In particular, fluorescent emission at 520 nm will vary at excitation frequencies 350 nm and 385 nm depending on the extent of calcium binding, so that the ratio of fluorescent emission intensity occurring as the result of excitation at these two frequencies is a sensitive measure of the intracellular calcium concentration.

Calcium leak channel current may be measured in cultured cells using patch clamp techniques as described in Fong et al. (1990) *Science* 250:673–676, the disclosure of which is incorporated herein by reference. A detailed protocol is set forth in the experimental section hereinafter. Such measurement of leak channel current will be particularly useful as a secondary screen for compounds which have been able to reduce intracellular calcium concentrations, e.g., by the fura-2 assays described above. Compounds which are found to both reduce intracellular calcium concentration and inhibit leak channel activity are particularly suitable for use in the present invention.

Another screen useful for identifying dihydropyridine derivatives in accordance with the present invention relies on the measurement of protein degradation in cultured cells, as described in Turner et al. (1988) *Nature* 335:735–738. Cultured cells are manipulated to increase intracellular calcium concentration in the presence and absence of the test compound. Successful test compounds are those which are able to lower intracellular free calcium and thereby inhibit protein degradation.

Dihydropyridine derivatives according to the present invention will be useful for both in vitro and in vivo applications. Suitable in vitro applications include the inhibition of proteolysis in cultured cells.

The dihydropyridine derivatives of the present invention will find their greatest use in vivo applications where they will be incorporated in pharmaceutical compositions. Such pharmaceutical compositions will comprise the dihydropyridine derivative and a pharmaceutically acceptable carrier. Such pharmaceutical compositions should contain a therapeutic amount of at least one compound according to the present invention, where the pharmaceutically acceptable carrier can be any compatible, non-toxic substance suitable to deliver the compound(s) to an intended host. Sterile water, alcohol, fats, waxes, and inert solids may be used as the carrier. Pharmaceutically acceptable adjuvants, buffering agents, dispersing agents, and the like, may also be incorporated into the pharmaceutical compositions. Preparation of pharmaceutical compositions incorporating active agents is well described in the medical and scientific literature. See, for example, Remington's Pharmaceutical Sciences, Mack Publishing Company, Easton, Pa., 16th Edition, 1982, the disclosure of which is incorporated herein by reference.

The pharmaceutical compositions just described are suitable for systemic administration to the host, including both parenteral and oral administration. Pharmaceutical compositions may be administered parenterally, i.e. subcutaneously, intramuscularly, or intravenously. Thus, the present invention provides compositions for administration to a host, where the compositions comprise a pharmaceutically acceptable solution of the dihydropyridine derivative compound in an acceptable carrier, as described above.

The concentration of the dihydropyridine derivative compound in the pharmaceutical carrier may vary widely, i.e. from less than about 0.1% by weight of the pharmaceutical composition to about 20% by weight, or greater. Typical pharmaceutical compositions for intramuscular injection would be made up to contain, for example, 1 ml to 4 ml of sterile buffered water and 1 μg to 200 mg of the dihydropyridine derivative.

The pharmaceutical compositions of the present invention will be administered in vivo to a mammalian host, particularly a human host suffering from or at risk of suffering from a pathogenic condition related to elevated levels of intracellular calcium. Such conditions include muscular dystrophy, hypertension, traumatic brain injury, stroke, Alzheimer's disease, and the like. The pharmaceutical compositions will be administered in amounts sufficient to reduce or alleviate such a pathogenic condition, where an amount adequate to accomplish this result is defined as a "therapeutically effective dose." Such therapeutically effective doses will depend on the extent of the disease, the size of the host, and the like, but will generally range from about 0.01 mg to 100 mg of the dihydropyridine derivative per kilogram of body weight of the host, with dosages of from 1 μg to 10 mg per kilogram being more commonly employed.

The following examples are offered by way of illustration, not by way of limitation.

EXPERIMENTAL

Materials and Methods

Cell Culture Medium and Experimental Solutions

| Proliferation Medium (PM): | |
| --- | --- |
| Hams F10 Medium | 154 ml |
| Chick Embryo Extract (2%) | 4 ml |
| Fetal Bovine Serum (20%) | 40 ml |
| Penicillin-Streptomycin (100) | 2 ml |
| | 200 ml |
| Differentiation Medium (DM): | |
| Dulbecco's Modified Eagles Medium | 193 ml |
| Horse Serum (2.5%) | 5 ml |
| Penicillin-Streptomycin (100X) | 2 ml |
| | 200 ml |
| Fura-2 Loading Solution: | |
| Puck's Saline ($Ca^{+2}$-Free) | 36.728 ml |
| Fetal Bovine Serum | 3.2 ml |
| $CaCl_2$ (1M) | 72 μl |
| | 40 ml |
| Rodent Saline Solution Components (mM): | |
| NaCl | 138.0 |
| KCl | 2.7 |
| $MgCl_2$ | 1.06 |
| $CaCl_2$ | 1.8 |
| Glucose | 5.6 |
| HEPES | 12.4 |
| ($pH_o$ = 7.28) | |

Myotube Cultures

The following culture methods were modified from Fong et al., (1990) *Science* 250:673–676. Mouse hindlimb muscle was dissected out and minced in Puck's saline. The tissue was then digested in 0.2% collagenase A (Sigma) for 1 hour at 37° C., spun down at low speed, then resuspended in 0.025% trypsin for 1 hour at 37° C. Afterwards, the tissue was triturated 10 times and spun at low speed. The supernatant was filtered with nylon mesh, into 10 ml of inhibitor media (IM, containing Puck's plus 20% fetal bovine serum (FBS) to stop the trypsin reaction). This supernatant, which contains the muscle satellite cells, was pelleted at high speed for 5 minutes, then resuspended in a total of 40 ml of PM. This cell suspension was plated onto eight 60 ml plastic tissue culture dishes, 5 ml per dish, which were coated overnight with 0.01% collagen type IV (Sigma). The next day the cells were washed once with Puck's Saline to remove cellular debris, and then returned to PM.

After 3 to 4 days of proliferation, the myoblasts were trypsinized for about 5 minutes (in which time most myoblasts have fallen off but most fibroblasts are still attached), then resuspended in 3 ml of IM and triturated 10 times with a 5 ml pipette. The cell suspensions from all eight dishes were collected and spun at high speed for 5 minutes. The pellet was resuspended in DM and triturated 20 times. This cell suspension is plated at 200,000 cells/ml (150,000 cells/ml for normal, due to lower fibroblast numbers) and plated at 1 ml per dish onto plastic or glass bottomed 35 ml dishes which were coated overnight with 0.01% collagen type IV. Another 1 ml was added per dish after the cells have settled about 10 minutes. After 16 to 24 hours, the cells were refed with DM containing 5 μM cytosine arabinosidase (ara-c) to control fibroblast and endothelial cell proliferation. The cultures were refed every 3 to 4 days, and were removed from ara-c one or two days before use in experiments.

Patch Clamp Methods

Single channel measurements were made using conventional patch-clamp techniques (Hamill et al. (1981) *Pleugers Arch.* 391:85–100), modified as previously described (Fong et al., (1990), supra, and Turner et al., (1991) *J. Cell. Biol.* 115:1701–1712). Briefly, Drummond microcap glass electrodes were pulled and fire polished to resistances of 5 to 10 MΩ, and coated with Sylgard (Dow Corning, Midland, Mich.). Cell-attached patches were made by touching the pipette to the cell and applying slight negative pressure, yielding seal resistances of 1 GΩ to 30 GΩ. Occasionally, seals were excised and interfaced with the air to form inside out patches. Data were acquired using an Axopatch 1-D amplifier (Axon Instruments, Foster City, Calif.) interfaced to an IBM AT-compatible computer with a Techmar AD/DA board (Scientific Solutions, Solon, Ohio). Data were filtered at two kHz using a −3dB, four-pole Bessel low-pass filter, and acquired using the Axotape program (Axon Instruments), with a sampling rate of 1500 points per second, for 60 seconds. Data were analyzed using the fetchan routine of pClamp (Axon Instruments), with filtering at 1 kHz. The pipette filling solution contained 96 mM $BaCl_2$, 12.4 mM Hepes, pH 7.2 (titrated with BaOH2). The bath solution contained (in mM): NaCl 138, KCl 2.7, $MgCl_2$ 1.06, $CaCl_2$ 0.18, glucose 5.6, Na-Hepes 12.4, pH 7.2. Low calcium was used to prevent spontaneous contractions of the myotubes. Cell culture media were removed previous to each experiment by washing 5 times with bath solution. All solutions were filtered through 0.22 μM filters. Experiments were performed at room temperature (approximately 25° C.).

For drug experiments, 3 to 5 minutes of activity was recorded, then the drug was added by perfusion into the chamber. The open probability of the channel was calculated for each minute interval, and plotted against time. A decrease in the open probability in the presence of the drug was expected of effective drugs.

Manganese Assay

Manganese influx rates were calculated by measuring the rate of loss of intensity of fura-2 (see below) at 357 nm wavelength after the addition of 50 mM $Mn^{+2}$. Fura-2 is not responsive to changes in calcium concentration at 357 nm wavelength. Rate of intensity loss is proportional to the permeability of the cell to $Mn^{+2}$, and by inference, a calcium-permeable pathway (see, e.g., Luckhoff and Clampham (1992), *Nature* 355:356–358).

Assay for Effect of Test Compounds on Intracellular Free Calcium

Normal and mdx myotubes were typically 6 to 12 days in differentiation conditions when used in assessment of 1,4-dihydropyridine drugs for their effect on intracellular free calcium ($[Ca^{2+}]i$). Myotubes can be seen after 24 hours in differentiation medium although we allowed a brief period for maturation. At the time of 1,4-dihydropyridine drug testing, all myotubes were able to illicit a calcium transient response to 100 mM carbachol, which is a nonhydrolyzable acetylcholine analogue, indicating that they were morphologically and biochemically differentiated. In addition, dystrophin-deficient myotubes showed an abnormally high level of resting $[Ca^{+2}]i$ compared to normal myotubes. Two methods were employed to evaluate the effect of 1,4-dihydropyridine drug analogues on myotube $[Ca^{+2}]i$ control (see below).

1. Fura-2AM Loading

Myotubes were loaded with fura-2AM for 1 to 1.5 hours at room temperature in the dark. Following fura-2 loading, myotubes were washed several times to remove unincorporated dye from the cells and myotubes were allowed to incubate on the microscope stage for approximately 15 minutes at 34° C. before calcium measurements were made. Myotubes were washed and bathed in rodent saline solution with 1.8 mM calcium, pH 7.28.

2. Rapid Drug Screening

All drugs were rapidly screened for their effect on resting $[Ca^{+2}]i$. At Time 0 minutes, a chosen group of myotubes had resting $[Ca^{+2}]i$ levels recorded. Afterwards, one myotube was selected and rodent saline solution with the test drug at 5 μM or 10 μM completely replaced the original saline solution. This marked the beginning of drug incubation with the myotubes. Resting $[Ca^{+2}]i$ levels were recorded after 15 minutes (or longer) from the same group of myotubes measured at time 0 minutes. An evaluation of the test drug effect on $[Ca^{30\ 2}]i$ was possible both on the individual myotube level and on a population basis. A test drug was expected to decrease myotube resting $[Ca^{30\ 2}]i$ levels if it was capable of modulating the calcium leak channel.

3. Drug Preincubation

Test drugs that reduced $[Ca^{30\ 2}]i$ in myotubes were further tested by long term incubation (3 hours) with myotubes to determine the effect of the drug on calcium levels and to determine the lowest concentration of drug needed to decrease mdx $[Ca^{30\ 2}]i$ towards normal levels. Normal and mdx myotubes were exposed to the test drug for a minimum of 3 hours by incubating the cells with the test drug for 1.5 hours in differentiation medium and for 1.5 hours in loading solution. The test drug was also present in rodent saline solution when calcium measurements were done. The test drug was prepared by diluting the drug stock (50 mM) to various concentrations ranging from a high of 10 μM, to a low of 0.1 μM with differentiation medium, loading solution, or rodent saline solution. Drugs were tested at 1 mM and at lower concentrations to determine their strength at reducing $[Ca^{30\ 2}]i$.

Dihydropyridine Derivatives

Dihydropyridine derivatives were tested for their ability to reduce resting free intracellular calcium levels in the cultured myotubes. The derivatives are represented by the general formula II:

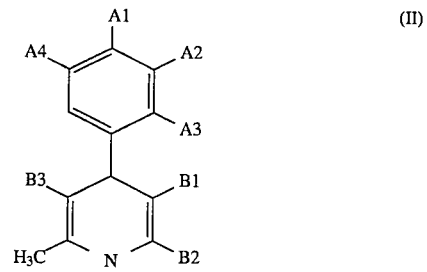

with specific compounds being identified in Table 1.

TABLE 1

| Compound | A1 | A2 | A3 | A4 |
|---|---|---|---|---|
| 1 | H | $NO_2$ | H | H |
| 2 | H | $NO_2$ | H | H |
| 3 | H | $NO_2$ | H | H |
| 4 | H | $NO_2$ | H | H |
| 5 | H | =N—O—N=[1] | — | H |
| 6 | H | —O—$CH_2CH_2$—O—[1] | — | H |
| 7 | —O—$CH_2CH_2$—O—[2] | — | H | H |
| 8 | H | H | H | H |
| 9 | H | $CH_3$ | H | H |
| 10 | H | Br | H | H |
| 11 | $CF_3$ | H | H | H |
| 12 | $OCH_2O$ | H | H | H |
| 14 | H | H | NCS | H |
| 15 | H | H | $NO_2$ | Cl |
| 16 | H | H | H | H |
| 17 | H | H | $N(CH_3)_2$ | H |
| 18 | H | $NO_2$ | H | H |
| 19 | H | OH | H | H |
| 20 | H | $NH_2$ | H | H |
| 21 | H | H | $OCH_2CHCH_2$ | H |
| 22 | H | H | $NO_2$ | H |

TABLE 1-continued

| | | | | |
|---|---|---|---|---|
| 23[3] | H | CF$_3$ | H | H |
| 24[3] | H | H | H | H |
| 25[4] | H | H | CF$_3$ | H |
| 26[5] | H | H | CF$_3$ | H |
| 27 | H | H | CF$_3$ | H |
| 28[6] | — | — | — | — |
| 29[7] | H | H | H | NO$_2$ |
| 30[8] | H | H | H | NO$_2$ |
| 31 | Cl | H | H | H |
| 32 | Br | H | H | H |
| 33 | OCH$_2$φ | H | H | H |
| 34 | CH$_3$ | H | H | H |
| 35 | OCH$_3$ | H | H | H |
| 36 | OH | H | H | H |
| 37 | NH$_2$ | H | H | H |
| 38 | N(CH$_3$)$_2$ | H | H | H |
| 39 | H | N[9] | H | H |
| 40 | CN | H | H | H |
| 41 | H | CF$_3$ | H | H |
| 42 | H | H | CF$_3$ | H |

| Compound | B1 | B2 | B3 |
|---|---|---|---|
| 1 | CO$_2$CH$_2$CH$_3$ | CH$_2$SCH$_2$CH$_2$NHCHO | CO$_2$CH$_3$ |
| 2 | CO$_2$CH$_2$CH$_3$ | CH$_2$SCH$_2$CH$_2$NHCOCH$_3$ | CO$_2$CH$_3$ |
| 3 | CO$_2$CH$_2$CH$_3$ Fumarate (+) | CH$_2$SCH$_2$CH$_2$NH$_2$ | CO$_2$CH$_3$ |
| 4 | CO$_2$CH$_2$CH$_3$ Fumarate (−) | CH$_2$SCH$_2$CH$_2$NH$_2$ | CO$_2$CH$_3$ |
| 5 | CO$_2$CH$_2$CH$_3$ Fumarate | CH$_2$SCH$_2$CH$_2$NH$_2$ | CO$_2$CH$_3$ |
| 6 | CO$_2$CH$_2$CH$_3$ Fumarate | CH$_2$SCH$_2$CH$_2$NH$_2$ | CO$_2$CH$_3$ |
| 7 | CO$_2$CH$_2$CH$_3$ Fumarate | CH$_2$SCH$_2$CH$_2$NH$_2$ | CO$_2$CH$_3$ |
| 8 | CO$_2$CH$_2$CH$_3$ Chloride | CH$_2$SCH$_2$CH$_2$NH$_2$ | CO$_2$CH$_3$ |
| 9 | CO$_2$CH$_3$ | CH$_3$ | CO$_2$CH$_3$ |
| 10 | CO$_2$CH$_3$ | CH$_3$ | CO$_2$CH$_3$ |
| 11 | CO$_2$CH$_3$ | CH$_3$ | CO$_2$CH$_3$ |
| 12 | CO$_2$CH$_3$ | CH$_3$ | CO$_2$CH$_3$ |
| 14 | CO$_2$CH$_3$ | CH$_3$ | CO$_2$CH$_3$ |
| 15 | CO$_2$CH$_3$ | CH$_3$ | CO$_2$CH$_3$ |
| 16 | CO$_2$CH$_3$ | CH$_3$ | CO$_2$CH$_3$ |
| 17 | CO$_2$CH$_3$ | CH$_3$ | CO$_2$CH$_3$ |
| 18 | CO$_2$CH$_2$CH$_3$ | CH$_3$ | CO$_2$CH$_2$CH$_3$ |
| 19 | CO$_2$CH$_3$ | CH$_3$ | CO$_2$CH$_3$ |
| 20 | CO$_2$CH$_3$ | CH$_3$ | CO$_2$CH$_3$ |
| 21 | CO$_2$CH$_3$ | CH$_3$ | CO$_2$CH$_3$ |
| 22 | CN | CH$_3$ | CN |
| 23[3] | CO$_2$CH$_2$CH$^-$N(CH$_3$)CH$_2$φ | CH$_3$ | CO$_2$CH$_3$ |
| 24[3] | CO$_2$CH$_2$CH$^-$N(CH$_3$)CH$_2$φ | CH$_3$ | CO$_2$CH$_3$ |
| 25[4] | NO$_2$ | CH$_3$ | CO$_2$CH$_3$ |
| 26[5] | NO$_2$ | CH$_3$ | CO$_2$CH$_3$ |
| 27 | NO$_2$ | CH$_3$ | NO$_2$ |
| 28[6] | CO$_2$CH$_3$ | CH$_3$ | CO$_2$CH$_3$ |
| 29[7] | COO$^-$CH$_3$ | CH$_3$ | CO$_2$CH$_3$ |
| 30[8] | — | CH$_3$ | CO$_2$CH$_3$ |
| 31 | CO$_2$CH$_3$ | CH$_3$ | CO$_2$CH$_3$ |
| 32 | CO$_2$CH$_3$ | CH$_3$ | CO$_2$CH$_3$ |
| 33 | CO$_2$CH$_3$ | CH$_3$ | CO$_2$CH$_3$ |
| 34 | CO$_2$CH$_3$ | CH$_3$ | CO$_2$CH$_3$ |
| 35 | CO$_2$CH$_3$ | CH$_3$ | CO$_2$CH$_3$ |
| 36 | CO$_2$CH$_3$ | CH$_3$ | CO$_2$CH$_3$ |
| 37 | CO$_2$CH$_3$ | CH$_3$ | CO$_2$CH$_3$ |
| 38 | CO$_2$CH$_3$ | CH$_3$ | CO$_2$CH$_3$ |
| 39 | CO$_2$CH$_3$ | CH$_3$ | CO$_2$CH$_3$ |
| 40 | CO$_2$CH$_3$ | CH$_3$ | CO$_2$CH$_3$ |
| 41 | CO$_2$CH$_3$ | CH$_3$ | CO$_2$CH$_3$ |
| 42 | CO$_2$CH$_3$ | CH$_3$ | CO$_2$CH$_3$ |

[1]Spans A2 and A3.
[2]Spans A1 and A2.
[3]HCl salt.
[4](−) isomer.

TABLE 1-continued

[5] (+) isomer.
[6] Ferrocene substitution.
[7] Dimer.

[8] 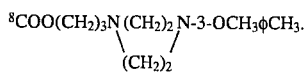

[9] Pyridyl.

RESULTS

Myotubes begin to form after 24 to 48 hours in differentiation medium. One to two weeks were allowed or myotube maturation before testing DHP drugs for their effect on $[Ca^{2+}]i$ modulation. At the time of drug testing, myotubes were able to illicit a calcium transient response to 100 μM carbachol (a nonhydrolyzable acetylcholine analogue), or to 100 mM extracellular KCL depolarization indicating that myotubes were morphologically and biochemically differentiated. In addition, dystrophin-deficient myotubes had abnormally high resting $[Ca^{2+}]i$ levels compared to normal. These were the basic myotube conditions required in order to proceed with drug testing.

Table 2 shows the effect of the test DHP compounds on myotube $[Ca^{2+}]i$ over a period covering 60 minutes. Compound no. 11 was identified as having a positive effect at lowering myotube $[Ca^{2+}]i$ after a 3 hour incubation and after short-term drug exposure. The effect of a brief exposure to compound no. 11 on myotube $[Ca^{2+}]i$ levels was investigated further, and it was found that short exposures to compound no. 11 caused $[Ca^{2+}]i$ to decrease in 44% (7/16 cases) of experiments. In addition, very small changes in $[Ca^{2+}]i$ occurred an equal number of cases under similar treatments. In contrast, myotube $[Ca^{2+}]i$ increased slightly in only 2 cases. As a control, the addition of nifedipine (50μM) caused $[Ca^{2+}]i$ levels to greatly increase over the same time period. The effect of nifedipine on myotube resting $[Ca^{2+}]i$ levels show that short-term drug testing is feasible for rapidly evaluating calcium responses to DHP compounds. The results from Table 2 show that compound no. 11 is capable of lowering myotube resting $[Ca^{2+}]i$.

To address the possibility that Fura-2 is interacting with compound no. 11 causing abnormal fluorescence intensities resulting in erroneous low calcium readings, we made two nominally calcium-free rodent saline solutions with 60 μM fura-2 salt containing either 60 μM compound no. 11 or DMSO. After 15 minutes of incubation at 23° C., fura-2 fluorescence intensities were measured at 345 nm and 385 nm excitation wavelengths. The fura-2 excitation intensities were unaffected by the presence of compound no. 11 indicating that it is not altering fura-2 and causing erroneous calcium measurements in myotubes.

Compounds nos. 32, 33, 34 and 38 also showed significant activity in lowering R. All results are set forth in Table 2.

TABLE 2

| Test Compound | Concentration | Time Period | Result |
|---|---|---|---|
| 1 | 12.5 μM | 30 min. | R increased. |
| 2 | 12.5 μM | 30 min. | Large increase in R. |
|  | 12.5 μM | 30 min. |  |
| 3 | 12.5 μM | 30 min. | R increased. |
| 4 | 12.5 μM | 50 min. | R increased. |
| 5 | 12.5 μM | 30 min. | R increased. |
| 6 | nM levels | 30 min. | R increased. |
| 7 | 12.5 μM | 30 min. | R increased. |
| 8 | 12.5 μM | 30 min. | R unchanged relative to control. |
|  | 12.5 μM | 30 min. |  |
| 9 | 12.5 μM | 30 min. | R increased. |
| 10 | 12.5 μM | 30 min. | R unchanged relative to control. |
| 11 | 1.25 μM | 60 to 90 min. | Significantly lowered R. |
| 12 | 12.5 μM | 30 min. | R increased. |
|  | 12.5 μM | 30 min. | R increased. |
| 14 | 12.5 μM | 30 min. | R increased. |
| 15 | 12.5 μM | 30 min. | R increased. |
| 16 | — | — | Not tested. |
| 17 | 12.5 μM | 30 min. | R increased. |
| 18 | 5 μM | 30 min. | R increased. |
| 19 | 5 μM | 30 min. | R increased. |
| 20 | 10 μM | 30 min. | R unchanged relative to control. |
| 21 | 5 μM | 30 min. | R unchanged relative to control. |
| 22 | 5 μM | 30 min. | R increased. |
| 23 | — | — | Not tested. |
| 24 | 5 μM | 30 min. | R increased. |
| 25 | 5 μM | 30 min. | R unchanged relative to control. |
| 26 | — | — | Not tested. |
| 27 | — | — | Not tested. |
| 28 | 3.3 μM | 30 min. | R increased. |
| 29 | 3.3 μM | 30 min. | R increased. |
| 30 | 5 μM | 30 min. | R increased. |
| 31 | 2 μM | 30 min. | R unchanged relative to control. |
| 32 | 2 μM | 30 min. | R significantly lowered. |
| 33 | 2 μM | 30 min. | R significantly lowered. |
| 34 | 2 μM | 30 min. | R significantly lowered. |
| 35 | 2 μM | 30 min. | R unchanged relative to control. |
| 36 | 2 μM | 30 min. | R unchanged relative to control. |
| 37 | 2 μM | 30 min. | R unchanged relative to control. |
| 38 | 2 μM | 30 min. | R significantly lowered. |
| 39 | 2 μM | 30 min. | R unchanged relative to control. |
| 40 | 2 μM | 30 min. | R lowered. |
| 41 | 2 μM | 30 min. | R unchanged relative to control. |
| 42 | 2 μM | 30 min. | R unchanged relative to control |

Although the foregoing invention has been described in detail for purposes of clarity of understanding, it will be obvious that certain modifications may be practiced within the scope of the appended claims.

What is claimed is:

1. A method for determining whether a test compound inhibits calcium leak channel activity in cells, said method comprising:

culturing myotubes under conditions where intracellular calcium concentrations depend on calcium leak channel activity; and measuring intracellular calcium concentrations in the cultured myotubes in the presence and absence of the test compound to determine whether the intracellular calcium concentration in the myotubes cultured in the presence of the test compound is lower than the intracellular calcium concentration in the myotubes cultured in the absence of the test compound, wherein a test compound which lowers said calcium concentration is considered to be a calcium leak channel inhibitor.

2. A method as in claim 1, wherein said test compound is a dihydropyridine compound.

3. A method as in claim 1, wherein said myotubes are dystrophic.

4. A method as in claim 1, wherein intracellular calcium concentration is measured by observing a change in fluorescence of a calcium sensitive dye which is introduced to the cultured myotubes prior to the test compound.

* * * * *